US00PP34615P2

(12) United States Plant Patent
Cho

(10) Patent No.: US PP34,615 P2
(45) Date of Patent: Sep. 27, 2022

(54) ***COLOCASIA* PLANT NAMED 'WAIKIKI'**

(50) Latin Name: *Colocasia esculenta*
Varietal Denomination: Waikiki

(71) Applicant: John J. Cho, Kula, HI (US)

(72) Inventor: John J. Cho, Kula, HI (US)

( * ) Notice: Subject to any disclaimer, the term of this patent is extended or adjusted under 35 U.S.C. 154(b) by 0 days.

(21) Appl. No.: 17/496,348

(22) Filed: Oct. 7, 2021

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 6/00; A01H 5/00
See application file for complete search history.

*Primary Examiner* — Keith O. Robinson
(74) *Attorney, Agent, or Firm* — Weatherly IP Solutions, LLC; James M. Weatherly

(57) ABSTRACT

A new variety of *Colocasia* plant named 'Waikiki' that is characterized by a clumping growth habit and large glossy green and variegated leaves with slightly undulating margins which are borne on glossy dark purple petioles. The color of the variegation of the first leaves to unfurl is predominantly cream-yellow, becoming increasingly infused and replaced by red-purple coloration as the leaves develop and age.

2 Drawing Sheets

Figure 1:
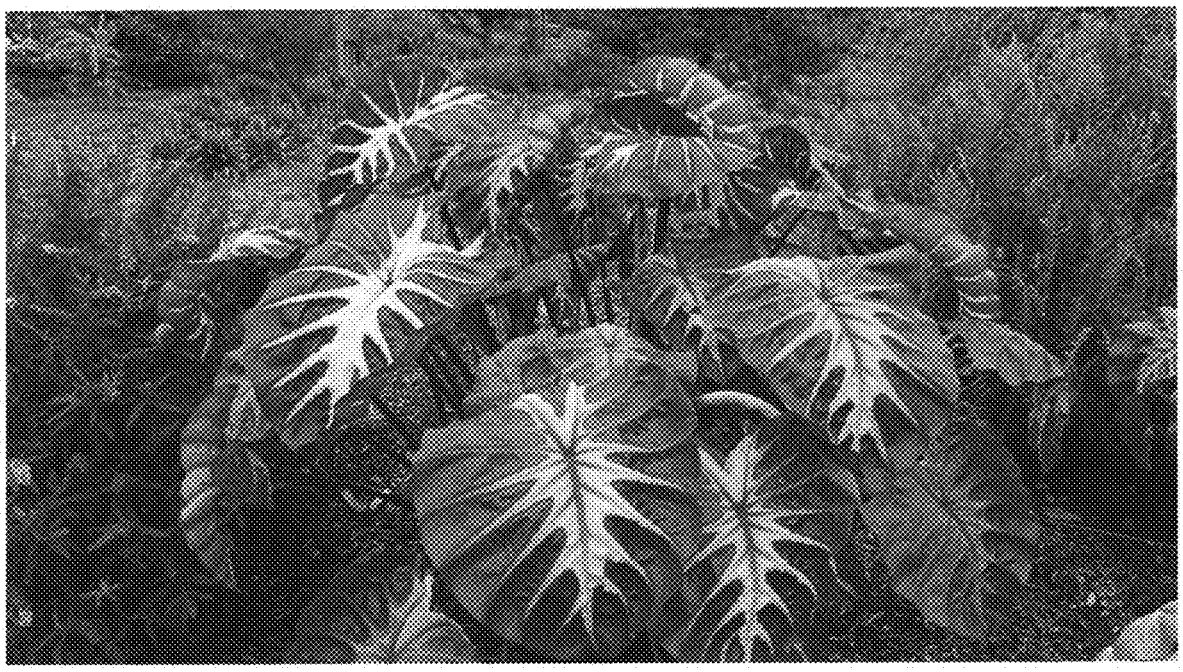

Genus and species: *Colocasia esculenta.*
Variety denomination: 'Waikiki'.

BACKGROUND OF THE NEW PLANT

The present invention relates to a new and distinct variety of *Colocasia* commonly known as the taro plant or elephant ears. *Colocasia* is grown as a food crop or for use as an ornamental plant for planting in containers or in the landscape. The new variety is known botanically as *Colocasia esculenta* and will be referred to hereinafter by the variety name 'Waikiki'.

*Colocasia* is a tuberous rooted perennial which is native to tropical Asia. It grows to 1.5 m. to 2 m. in height from starchy tubers. The leaves of *Colocasia* are heart-shaped and very large. The tuberous roots are cooked and eaten as a starchy staple in many tropical areas. *Colocasia* are also grown as an ornamental plant for the landscape in warmer climates or as a summer container plant in colder areas.

The new *Colocasia* variety named 'Waikiki' is the product of a long-term breeding program carried out by the inventor in a cultivated area in Kula, Hi. The purpose of the breeding program is to develop new commercial varieties by combining attributes of plant vigor with novel leaf coloration and color combinations, and leaf texture.

'Waikiki' is a seedling selection from the controlled pollination carried out by the inventor between the inventor's variety of *Colocasia* Plant Named 'White Lava' (U.S. Plant Pat. No. 24,481) as female parent and the inventor's unreleased and unnamed *Colocasia* seedling selection denominated as '9-14' as male parent.

The inventor selected 'Waikiki' for the striking variegation pattern and coloration of its foliage, for its naturally vigorous branching and clumping growth habit and for its glossy dark purple petioles.

The most commonly employed means of asexual propagation of the genus *Colocasia* is the excision and replanting of a shoot which consists of the apical 1 cm. to 2 cm. portion of the plant corm with the attached basal 15 cm. to 20 cm. portion of the petiole. In regions of the world where *Colocasia* is grown, this plant shoot is known as a "huli", and the means of propagation is known as "huli propagation". The first asexual propagation of 'Waikiki' was carried out by the inventor in Kula, Hi. in 2018 using this method of "huli propagation". Subsequent asexual reproductions by huli propagation and by tissue culture have confirmed to the inventor 'Waikiki' is stable and uniform, and reproduces true to type in successive generations of asexual propagation.

SUMMARY

The following traits have been repeatedly observed and represent the distinguishing characteristics of the new *Colocasia* variety named 'Waikiki'. 'Waikiki' has not been tested under all possible conditions and phenotypic differences may be observed with variations in environmental, climatic and cultural conditions, however, without any variance in genotype:

1. 'Waikiki' grows with a clumping habit, achieving a mature height of 1.0-1.2 m. and spread of 2 m. when grown in moist soils.
2. 'Waikiki' exhibits large sagittate leaves with undulating margins.
3. The leaves of 'Waikiki' are borne on glossy dark purple petioles.
4. The leaf tissue at and immediately adjacent to the petiole attachment, known as the piko, is red-purple in color on both surfaces.
5. The leaves of 'Waikiki' are glossy and medium green in color with bold contrasting variegation which changes in color as the leaf develops and ages from first opening or unfurling until senescence.
6. The leaves of 'Waikiki' open and unfurl with cream-colored variegation except for the color of the piko and the immediately adjacent veins which are red-purple in color.

7. A mature leaf of 'Waikiki' exhibits pale cream variegation with contrasting red-purple coloration of the principal veins which red-purple coloration extends further into the cream variegated tissue as the leaf ages.
8. A leaf of 'Waikiki' which is approaching senescence exhibits predominantly pale red-purple variegation with darker mid red-purple coloration along the principal veins.

DESCRIPTION OF THE PHOTOGRAPHS

The accompanying color photographs illustrate the overall appearance of 'Waikiki' showing the colors as true as it is reasonably possible to obtain in colored reproductions of this type. Colors in the photographs may differ from the color values cited in the detailed botanical description, which accurately describe the actual colors of the new variety 'Waikiki'.

Both photographs were taken in August 2020 from a 13 month old plant from planting which was growing outdoors in Raleigh, N.C. The illustrated plant was planted as a young liner plant in July 2019 and has not received any winter protection or been treated with any plant growth regulators.

The photograph labeled as FIG. 1 shows a mature plant of 'Waikiki' and depicts the clumping plant habit, the glossy dark purple petioles and the changing coloration of the variegation as each leaf opens and matures.

Figure 2:
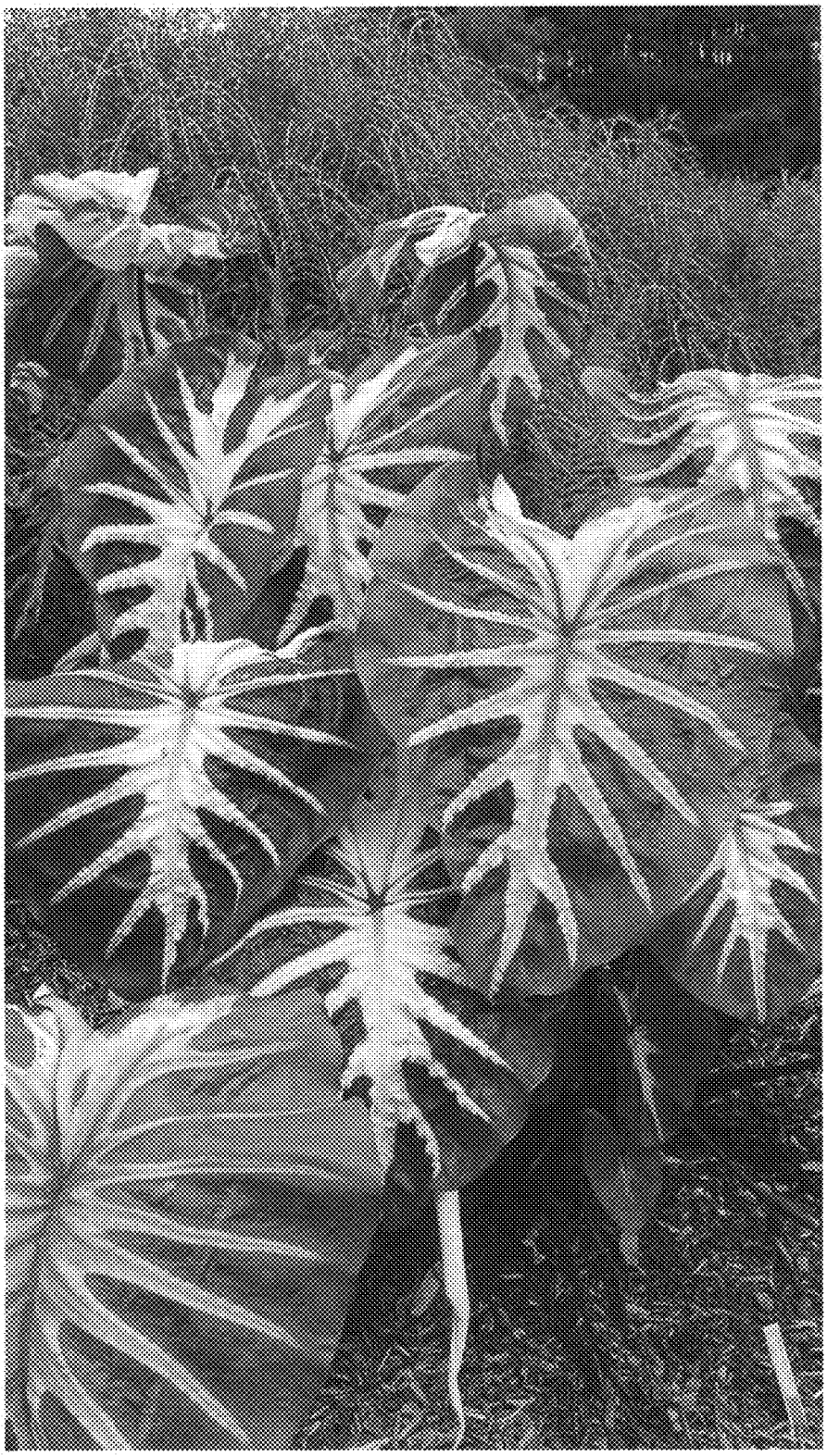

The photograph labeled as FIG. 2 shows a close-up view of the leaves of 'Waikiki' at various stages of development.

DESCRIPTION OF THE NEW VARIETY

The following is a detailed description of the new *Colocasia* plant named 'Waikiki'. Data was collected from a plant which was 13 months old from planting a young liner plant. The observed plant was planted and grown out of doors in Raleigh, N.C. The color determinations are in accordance with the 2007 edition of The Royal Horticultural Society Colour Chart, London, England, except where general color terms of ordinary dictionary significance are used. The growing requirements are similar to other *Colocasia*.

Botanical classification:

*Genus.*—*Colocasia.*

*Species.*—*Esculenta.*

*Denomination.*—'Waikiki'.

*Common name.*—Taro or elephant ears.

Plant:

*Plant use.*—Container or landscape plant.

*Cultural requirements.*—Cultural requirements are well draining soil or growing media, full sun to partial shade.

*Roots.*—System type: Tuberous. Dimensions: 18 cm to 20 cm in length, 8 cm to 10 cm in diameter. Color: 155B.

*Corm.*—Color: 155B. Texture: Firm. Shape: Cylindrical. Diameter: 127.0 mm to 135.0 mm. Length: 58.0 mm to 62.0 mm.

*Plant vigor.*—Vigorous, prolific basal shoot production.

*Plant growth habit.*—Upright, non-spreading.

*Plant growth rate and crop time.*—A two-gallon container plant grown at 18° C. to 20° C. may be produced in approximately 16-20 weeks from planting a rooted plug or liner which has been grown for approximately 12 weeks from initial planting as a tissue cultured division or explant.

*Plant dimensions* (*2-gallon container plant*).—50-60 cm. in height, 40-50 cm. in width.

*Plant dimensions* (*mature plant in the landscape*).—1.0-1.2 m. in height, 2 m. in width.

*Plant hardiness.*—USDA Zone 7b.

*Propagation.*—Propagation is accomplished by huli propagation and by tissue culture.

*Pest or disease susceptibility and resistance.*—'Waikiki' has not been found to be more or less susceptible to disease or pests than other cultivars of the genus. No resistance or susceptibility to disease or pests have been observed.

Parentage:

*Female parent.*—*Colocasia* 'White Lava' (U.S. Plant Pat. No. 24,481).

*Male parent.*—*Colocasia* seedling selection '9-14' (unnamed and unreleased).

Foliage:

*Number.*—A mature plant of 'Waikiki' bears 25 to 30 opening and open leaves at one time; new leaves appear rapidly, around every 2 to 3 days, due to the profusion of new basal shoots.

*Petioles.*—Shape: Cylindrical. Length: 75 cm to 90 cm. Width: 8 mm (just below leaf attachment) increasing to 20 mm to 25 mm at the base. Color: 187A. Surface: Glossy. Strength: Medium.

*Leaf.*—Dimensions at maturity: 30 cm to 35 cm in length and 20 cm to 22 cm in width. Average leaf sinus depth: 8 cm to 10 cm. Aspect: Oblique, apex downwards. Shape: Sagittate. Margins: Entire, undulating between lateral veins. Apex: Acute. Base: Peltate. Attachment: Petiolate with characteristic tissue formed at junction of leaf blade with the upper termination of the petiole. This area of the leaf tissue is known as the "piko" and is evident by the upper and lower piko surface color being similar to the color of the petiole. The principal veins radiate from the piko. Piko color: 71A. Texture: Glossy (both surfaces). Leaf color (color of leaf ground, adaxial surface, all stages of development): Ranges between N134A and 135A. Leaf color (color of leaf ground, abaxial surface, new leaves unfurling): Initially slate grey N187A or lighter, becoming 138A-138B. Leaf color (color of leaf ground, abaxial surface, leaf expanded, all ages): Ranges between 138A and 138B. Leaf color (color of variegation, newly unfurled leaf, adaxial surface): Predominantly (90%-95% of variegation) cream-light yellow, between 155A and 8D, except for red-purple piko 71A and narrow rays of lighter red-purple 72D coloration extending along central and lateral veins. Leaf color (color of variegation, leaf unfurled for 5-7 days, adaxial surface): Prominent extension, widening and gradual infusion of red-purple veinal coloration 71A-72C becoming light red-purple 70C-70D nearest the veins. Leaf color (color of variegation, oldest leaves close to senescence, adaxial surface): Entirely red-purple 72B-72C, except broad veins darker red-purple 71A. Leaf color (color of variegation, abaxial surface, all stages of leaf development): Predominantly cream-light yellow, between 155A and 8D, except for red-purple piko 71A and narrow rays of lighter red-purple 72D coloration extending along central and lateral veins. Venation: Palmate. Veins: 3 principal veins radiate from the piko: one midrib extending from the piko to the leaf apex, one pair of veins extending towards each of the basal lobe margins. 7 to 8 pairs of approximately opposite secondary veins. Vein color (both surfaces): Ranges between 71A (nearest the piko) and 72D. Vein prominence: Depressed (adaxial surface), raised (abaxial surface).

Inflorescence, flowers and reproductive organs:

*Inflorescence*.—Not observed on container-grown plants. Occasionally observed on mature plants. The inflorescence consists of a short pale green peduncle, a spike or spadix which contains female flowers at the base and male flowers towards the apex, and an elongated pale yellow spathe which wraps tightly around the spadix.

*Seed*.—Seed is not produced naturally since male and female flowers within each inflorescence do not mature at the same time. Pollination can be achieved manually or in nature, only with the presence of small insect pollinators which are found in regions of genetic origin of the species, and not Hawaii.

COMPARISON TO PARENTAL LINES AND COMMERCIAL VARIETY

'Waikiki' may be compared to the female parent, *Colocasia* 'White Lava' by the color and surface of their leaves. Whereas the leaves of 'White Lava' are semi glossy, green with pale yellow variegation, the leaves of 'Waikiki' are glossy green with vibrant and contrasting cream-yellow and red-purple variegation.

'Waikiki' may be compared to the male parent, *Colocasia* selection '9-14', as follows. Whereas both varieties exhibit purple petioles, the leaves of '9-14' are matte and dark purple in color with a white central streak of variegation, and the leaves of 'Waikiki' are dark green in color with prominent cream and red-yellow variegation.

'Waikiki' may be compared to the commercial *Colocasia* 'Maui Sunrise' (U.S. Plant Pat. No. 31,175) by the color of their leaves. Whereas the leaves of 'Maui Sunrise' are a mid-green color with a prominent contrasting white to cream-yellow central streak, the leaves of 'Waikiki' are green with a vibrant and contrasting cream-yellow and red-purple variegation.

I claim:

1. A new and distinct cultivar of *Colocasia* Plant Named 'Waikiki' as described and illustrated herein.

* * * * *